US005769792A

United States Patent [19]
Palcic et al.

[11] Patent Number: 5,769,792
[45] Date of Patent: *Jun. 23, 1998

[54] ENDOSCOPIC IMAGING SYSTEM FOR DISEASED TISSUE

[75] Inventors: Branko Palcic; Calum E. MacAulay; Bruno W. Jaggi; Stephen C-T Lam, all of Vancouver, Canada; Amedeus E. Profio, Santa Barbara, Calif.; Jaclyn Y-C Hung, Parkville, Australia

[73] Assignee: Xillix Technologies Corp., Canada

[ * ] Notice: The term of this patent shall not extend beyond the expiration date of Pat. No. 5,507,287.

[21] Appl. No.: 632,018

[22] Filed: Apr. 15, 1996

Related U.S. Application Data

[63] Continuation of Ser. No. 428,494, Apr. 27, 1995, Pat. No. 5,507,287, which is a continuation of Ser. No. 82,019, Jun. 23, 1993, abandoned, which is a continuation of Ser. No. 725,283, Jul. 3, 1991, abandoned.

[51] Int. Cl.⁶ ........................................ A61B 6/00
[52] U.S. Cl. .......................... 600/477; 600/478; 356/318
[58] Field of Search .................... 128/633, 634, 128/664–666; 356/318; 250/341.1; 600/310, 317, 342, 473, 475–479

[56] References Cited

U.S. PATENT DOCUMENTS

| | | |
|---|---|---|
| 4,473,841 | 9/1984 | Murakoshi et al. . |
| 4,541,438 | 9/1985 | Parker et al. . |
| 4,556,057 | 12/1985 | Hiruma et al. . |
| 4,718,417 | 1/1988 | Kittrell et al. . |
| 4,719,508 | 1/1988 | Sasaki et al. . |
| 4,768,513 | 9/1988 | Suzuki . |
| 4,773,097 | 9/1988 | Suzaki et al. . |
| 4,774,568 | 9/1988 | Matsuo . |
| 4,786,813 | 11/1988 | Svanberg et al. . |
| 4,805,597 | 2/1989 | Iwakoshi . |
| 4,821,117 | 4/1989 | Sekiguchi . |

(List continued on next page.)

FOREIGN PATENT DOCUMENTS

| | | |
|---|---|---|
| 0215772 | 3/1987 | European Pat. Off. . |
| 58-12675 | 1/1983 | Japan . |
| 2-22331 | 6/1983 | Japan . |
| 2203831 | 10/1988 | United Kingdom . |
| 86/02730 | 5/1986 | WIPO . |
| 90/10219 | 9/1990 | WIPO . |
| 90/12536 | 11/1990 | WIPO . |

OTHER PUBLICATIONS

Alfano et al., "Fluorescence Spectra from Cancerous and Normal Human Breast and Lung Tissues," *IEEE Journal of Quantum Electronics,* vol. QE–23, No. 10, 1987, pp. 1806–1811.

Alfano et al., "Laser Induced Fluorescence Spectroscopy from Native Cancerous and Normal Tissue," *IEEE Journal of Quantum Electronics,* vol. QE–20, No. 12, Dec. 1984, pp. 1507–1511.

(List continued on next page.)

*Primary Examiner*—Ruth S. Smith
*Attorney, Agent, or Firm*—Christensen, O'Connor, Johnson & Kindness PLLC

[57] ABSTRACT

Apparatus for imaging diseases in tissue comprising a light source for generating excitation light that includes wavelengths capable of generating characteristic autofluorescence for abnormal and normal tissue. A fiber-optic illuminating light guide is used to illuminate tissue with light that includes at least the excitation light thereby exciting the tissue to emit the characteristic autofluorescence. An imaging bundle collects emitted autofluorescence light from the tissue. The autofluorescence light is filtered into spectral bands in which the autofluorescence intensity for abnormal tissue is substantially different from normal tissue and the autofluorescence intensity for abnormal tissue is substantially similar to normal tissue. An optical system is used to intercept the filtered autofluorescence light to acquire at least two filtered emitted autofluorescence images of the tissue. The acquired images are displayed in real time on a display monitor in such a manner as to delineate abnormal and normal tissue.

36 Claims, 7 Drawing Sheets

U.S. PATENT DOCUMENTS

| | | |
|---|---|---|
| 4,827,908 | 5/1989 | Matsuo . |
| 4,852,579 | 8/1989 | Gilstad et al. . |
| 4,858,001 | 8/1989 | Milbank et al. . |
| 4,860,731 | 8/1989 | Matsuura . |
| 4,867,137 | 9/1989 | Takahashi . |
| 4,868,647 | 9/1989 | Uehara et al. . |
| 4,930,516 | 6/1990 | Alfano et al. . |
| 4,938,205 | 7/1990 | Nudelman . |
| 4,957,114 | 9/1990 | Zeng et al. . |
| 4,993,404 | 2/1991 | Lane . |
| 4,998,972 | 3/1991 | Chin et al. . |
| 5,003,977 | 4/1991 | Suzuki et al. . |
| 5,042,494 | 8/1991 | Alfano . |
| 5,071,417 | 12/1991 | Sinofsky . |
| 5,078,150 | 1/1992 | Hara et al. . |
| 5,090,400 | 2/1992 | Saito . |
| 5,091,652 | 2/1992 | Mathies et al. . |
| 5,115,137 | 5/1992 | Andersson-Engels et al. . |
| 5,117,466 | 5/1992 | Buican et al. . |
| 5,125,404 | 6/1992 | Kittrell et al. . |
| 5,131,398 | 7/1992 | Alfano et al. . |
| 5,318,023 | 6/1994 | Vari et al. . |
| 5,318,024 | 6/1994 | Kittrell et al. . |
| 5,377,676 | 1/1995 | Vari et al. . |
| 5,421,337 | 6/1995 | Richards-Kortum et al. . |
| 5,507,287 | 4/1996 | Palcic et al. ............................ 128/665 |

OTHER PUBLICATIONS

Andersson–Engels et al., "Fluorescence Characteristics of Atherosclorotic Plaque and Malignant Tumors," *SPIE,* vol. 1426, 1991, pp. 31–43.

Andersson–Engels et al., "Tissue Diagnostics Using Laser–Induced Fluorescence," Ber Bunsenges, *Phys. Chem.,* vol. 93, 1989, pp. 335–342.

Coffey et al., "Evaluation of Visual Acuity During Laser Photoradiation Therapy of Cancer," *Lasers in Surgery and Medicine,* vol. 4, pp. 65–71.

Cothren et al., "Gastrointestinal Tissue Diagnosis by Laser–Induced Fluorescence Spectroscopy at Endoscopy," *Gastrointestinal Endoscopy,* vol. 36, No. 2, 1990, pp. 105–111.

Dougherty et al., "Cutaneous Phototoxic Occurrences in Patients Receiving Photofrin," *Lasers in Surgery and Medicine,* vol. 10, 1990, pp. 485–488.

Hayata et al., "Fiberoptic Bronchoscopic Laser Photoradiation for Tumor Localization in Lung Cancer," *Chest,* vol. 82, 1982, pp. 10–14.

Hirano et al., "Photodynamic Cancer Diagnosis and Treatment System Consisting of Pulse Lasers and an Endoscopic Spectro–Image Analyzer," *Laser in Life Sciences,* vol. 3(1), 1989, pp. 1–18.

Hung et al., "Autofluorescence of Normal and Malignant Bronchial Tissue," *Lasers in Surgery and Medicine,* vol. 11, 1991, pp. 99–105.

Ikeda, "New Bronichial TV Endoscopy System," Elsevier Science Publishers B.V. Biomedical Press, 1988.

Kapadia et al., "Laser–Induced Fluorescence Spectroscopy of Human Colonic Mucosa," *Gastroenterology,* vol. 99, 1990, pp. 150–157.

Kato et al., "Early Detection of Lung Cancer by Means of Hematoporphyrin Derivative Fluorescence and Laser Photoradiation," *Clinics in Chest Medicine,* vol. 6, No. 2, 1985, pp. 237–253.

Kato et al., Photodynamic Diagnosis in Respiratory Tract Malignancy Using an Excimer Dye Laser System, *Journal of Photochemistry and Photobiology,* B:Biology, vol. 6, 1990, pp. 189–196.

Lam et al., "Fluorescence Detection," *Advances in the Diagnosis and Therapy of Lung Cancer,* Blackwell Scientific Publications Inc.

Lam et al., "Fluorescence Imaging of Early Lung Cancer," *IEEE Eng. Med. Biology,* vol. 12, 1990.

Lam et al., "Detection of Lung Cancer by Ratio Fluorometry With and Without Photofrin II," *SPIE Proc.* vol. 1201, 1990, pp. 561–568.

Lam et al., Detection of Early Lung Cancer Using Low Dose Photofrin II, *Chest,* vol. 97, 1990, pp. 333–337.

Lam et al., "Mechanism of Detection of Early Lung Cancer by Ratio Fluorometry," *Lasers in Life Sciences,* vol. 4(2), 1991, pp. 67–73.

Montan et al., "Multicolor Imaging and Contrast Enhancement in Cancer–Tumor Localization Using Laser–Induced Fluorescence in Hematoporphyrin–derivative–bearing Tissue," *Optics Letters,* vol. 10(2), 1985, pp. 56–58.

Mullooly et al., "Dihematoporphyrin Ether–Induced Photosensitivity in Laryngeal Papilloma Patients," *Lasers in Surgery and Medicine,* vol. 10, 1990, pp. 349–356.

Palcic et al., "Development of a Lung Imaging Fluorescence Endoscope," Proceedings of the 12th Annual Int'l Conference of the IEEE Engineering in Medicine and Biology Society, vol. 12, No. 1, 1990.

Palcic et al., "The Importance of Image Quality for Computing Texture Features in Biomedical Specimens," *SPIE Proc.,* vol. 1205, 1990, pp. 155–162.

Palcic et al. "Lung Imaging Fluorescence Endoscope: A Device for Detection of Occult Lung Cancer," *Medical Design and Material,* 1991.

Palcic et al., "Lung Imaging Fluorescence Endoscope: Development and Experimental Prototype," *SPIE,* vol. 1448, 1991, pp. 113–117.

Palcic et al., "Detection and Localization of Early Lung Cancer by Imaging Techniques," *Chest,* vol. 99, 1991, pp. 742–743.

Peak et al., "DNA–to–Protein Crosslinks and Backbone Breaks Caused by FAR– and NEAR–Ultraviolet and Visible Light Radiations in Mammalian Cells," Mechanism of DNA Damage and Repair, Implications for Carcinogenesis and Risk Assessment, 1986, pp. 193–202.

Profio et al., "Digital Background Subtraction for Fluorescence Imaging," *Medical Physics,* vol. 13(5), 1988, pp. 717–727.

Profio et al., "Endoscopic Fluorescence Detection of Early Lung Cancer," *SPIE,* vol. 1426, 1991, pp. 44–46.

Profio et al., "Fluorometer for Endoscopic Diagnosis of Tumors," *Medical Physics,* vol. 11(4), 1984, pp. 516–520.

Profio et al., "Laser Fluorescence Bronchoscope for Localization of Occult Lung Tumors," *Medical Physics,* vol. 6, 1979, pp. 523–525.

Rava et al., "Early Detection of Dysplasia in Colon and Bladder Tissue Using Laser Induced Fluorescence," *SPIE,* vol. 1426, 1991, pp. 68–78.

Razum et al., "Skin Photosensitivity: Duration and Intensity Following Intravenous Hematoporphyrin Derivatives, $H_pD$ and DHE," *Photochemistry and Photobiology,* vol. 46, No. 5, 1987, pp. 925–928.

Richards–Kortum et al., "Spectroscopic Diagnosis of Colonic Dysplasia: Spectroscopic Analysis," *Biochemistry and Photobiology,* vol. 53, No. 6, 1991, pp. 777–786.

Tang et al., "Spectroscopic Differences Between Human Cancer and Normal Lung and Breast Tissues," *Lasers in Surgery and Medicine,* vol. 9, 1989, pp. 290–295.

Wagnieres et al., "Photodetection of Early Cancer by Laser Induced Fluorescence of a Tumor–Selective Dye: Apparatus Design and Realization," *SPIE Proc.,* vol. 1203, 1990, pp. 43–52.

Wooten et al., "Prospective Study of Cutaneous Phototoxicity After Systemic Hematoporphyrin Derivative," *Lasers in Surgery and Medicine,* vol. 8, 1988, pp. 294–300.

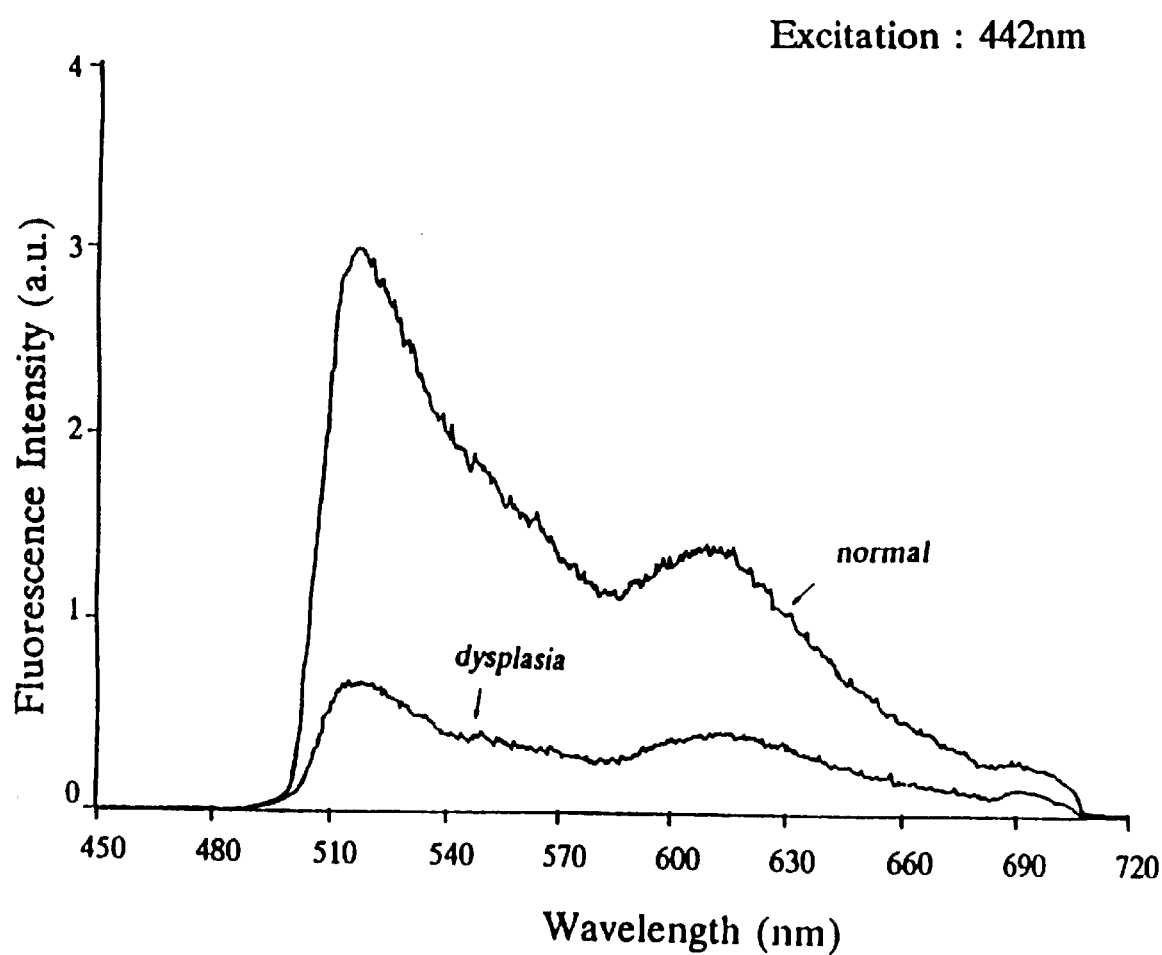

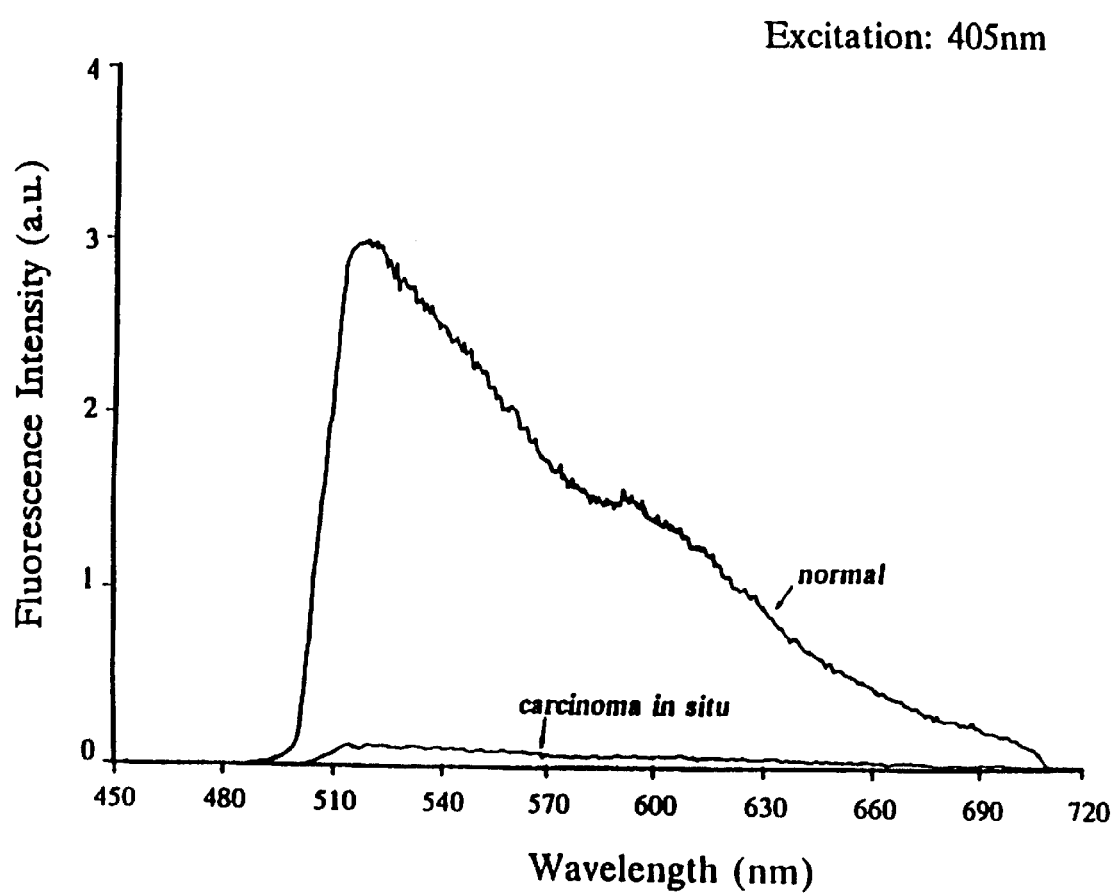

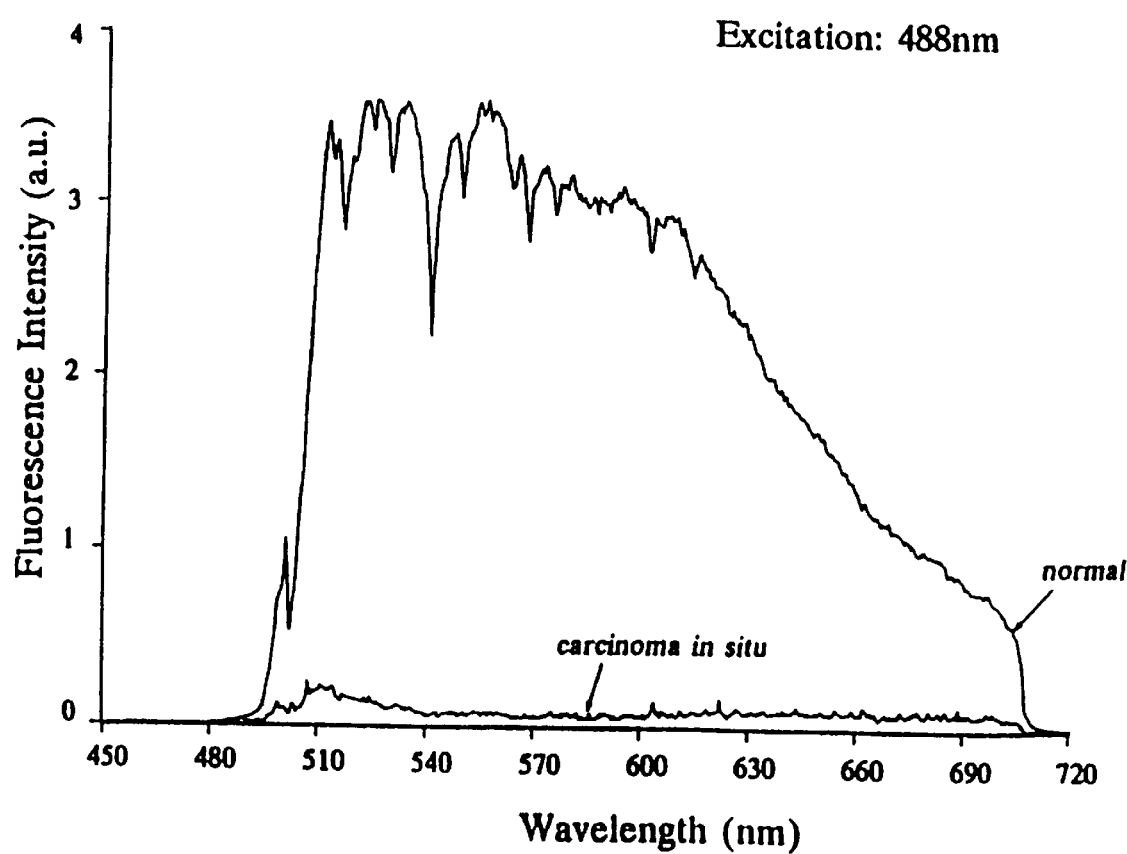

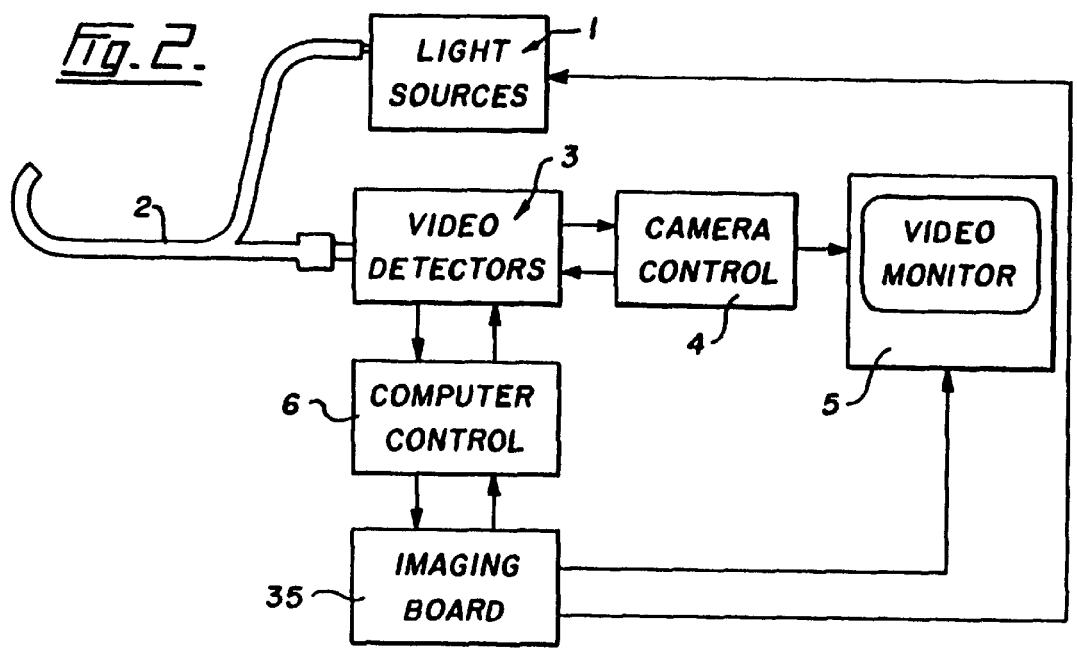
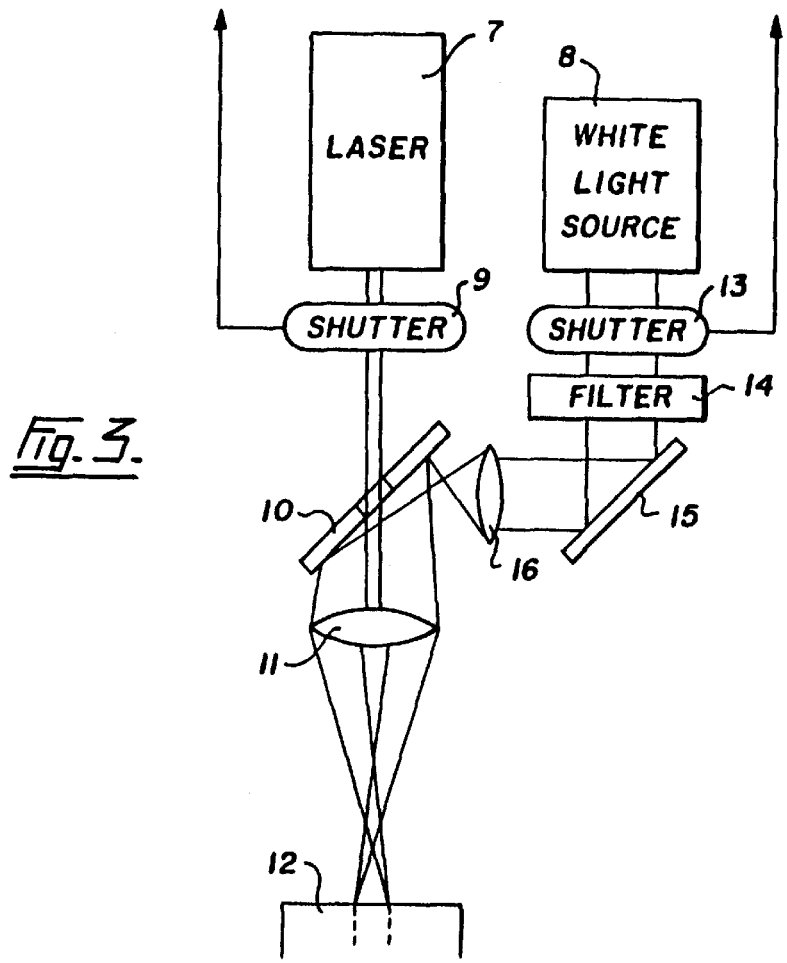

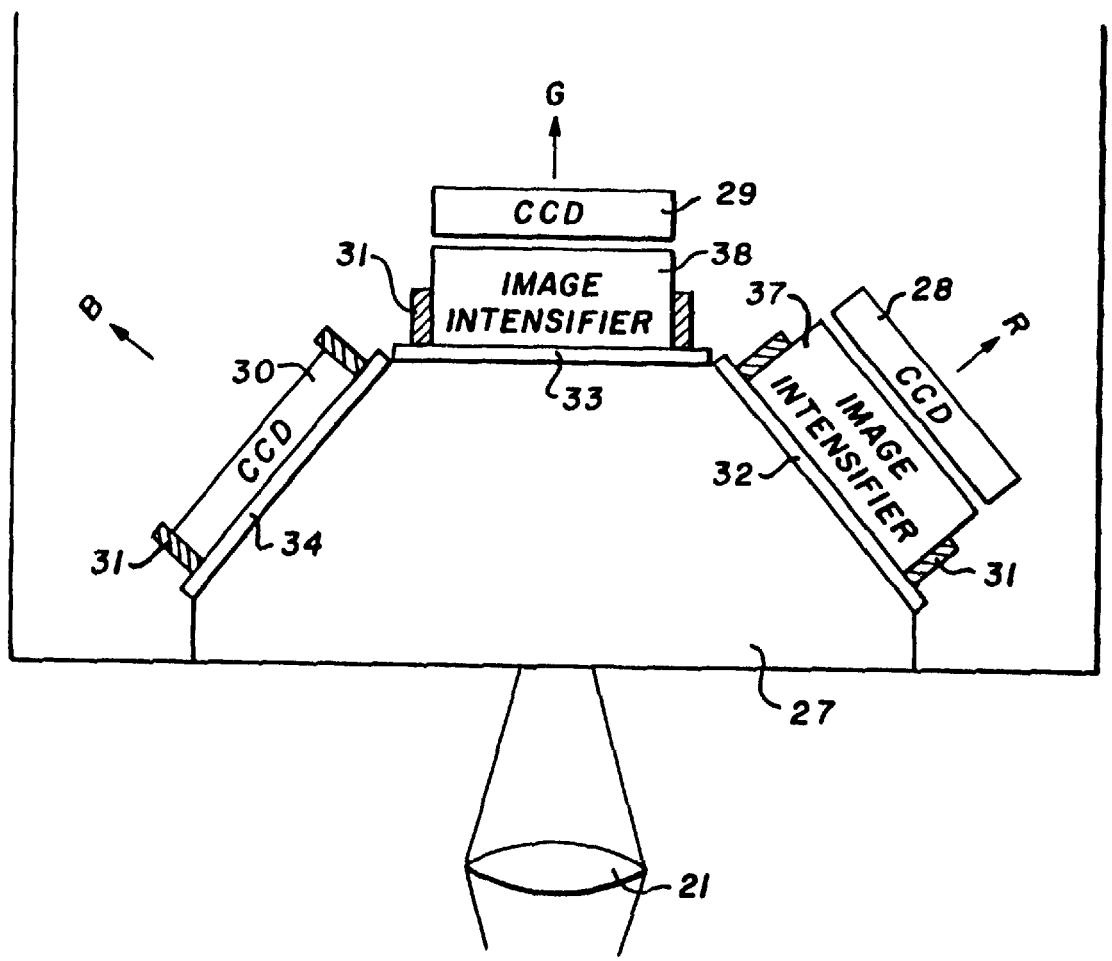

ENDOSCOPIC IMAGING SYSTEM FOR DISEASED TISSUE

RELATED APPLICATIONS

The present application is a continuation of our previous application Ser. No. 08/428,494, filed Apr. 27, 1995, now U.S. Patent No. 5,507,287, which was a continuation of application Ser. No. 08/082,019, filed Jun. 23, 1993, now abandoned which was a continuation of application Ser. No. 07/725,283, filed Jul. 3, 1991, now abandoned the benefit of the filing date of which is being claimed under 35 U.S.C. § 120, and which is herein incorporated by reference.

FIELD OF THE INVENTION

This invention relates to an apparatus for imaging abnormal tissues in the body to locate and identify areas that are otherwise not recognizable by white light endoscopy. The invention is particularly suited for imaging abnormal bronchial tissues to detect conditions such as inflammation, denudation, dysplasia and noninvasive early cancer (carcinoma in situ).

BACKGROUND OF THE INVENTIKON

At present, the most effective method for examination of body cavities in human patients is by endoscopes. For examination of the air passages of the lung, a flexible endoscope is usually used, commonly referred to as a bronchoscope. Bronchoscopes, like all endoscopes, employs visible white light to illuminate the surface under examination. The illuminating light is brought into the air passages (bronchi) of the lungs via a fiber-optic illuminating light guide. The reflected and scattered light from the bronchial tissues is captured by a projection lens which focuses the image into the bronchoscope's imaging bundle. The imaging bundle is composed of several thousand individually wrapped fibers, which transmit a coherent image to the exterior of the body. This image is then projected through the ocular of the bronchoscope for human observation. A color video camera can be attached to the eyepiece of the bronchoscope such that color images of scattered/reflected white (broadband) light can be viewed on a color video monitor.

Using a conventional bronchoscope, large invasive cancers can be readily seen. However, focal inflammation, denudation, dysplasia, and early lung cancers cannot be readily seen by such an apparatus.

Several methods have been developed to visualize small early lung cancers which are difficult to detect by ordinary white light bronchoscopy. All of these involve the use of tumor localizing drugs, e.g., Haematoporphyrin derivatives or Porfimer sodium, which have been shown to be preferentially retained in tumor tissues. Some of these drugs also fluoresce and their fluorescence can be detected by non-imaging and imaging devices (A.E. Proflo et al., *Med Phys.* 6:532–535, 1979; A.E. Proflo et al., *Med Phys.* 11:516–520, 1984; A.E. Profio et al., *Med Phys.* 13:717–721, 1986; Y. Hayata et al., *Chest* 82:10–14, 1982; A. Kato, D.A. Cortese, *Clin. Chest Med* 6:237–253, 1985; S. Montan et al., *Opt Letters* 10:56–58, 1985). The drawback of these techniques is the use of drugs which may have serious side effects and therefore may not be appropriate for diagnostic purposes. In addition, the use of non-imaging devices such as the ratio fluorometer probe (AE. Proflo et al., *Med Phys.* 11:516–520, 1984) cannot delineate the exact site and dimensions of the abnormal areas.

An alternative approach for detecting invasive tumors has been proposed by Alfano et al. in U.S. Pat. No. 4,930,516, issued Jun. 5, 1990. Alfano discloses a method of detecting cancers on the basis that the fluorescence spectra of cancerous tissues is different from normal tissues in that the maximal fluorescence peak of tumor tissues is blue shifted to lower wavelengths (from 531 nm to 521 nm). These observations were made based on in vitro measurements in excised, large (invasive) animal and human tumors but have not been reported on human tumors in vivo. In addition, there are no reports of other abnormal tissues such as inflamed or precancerous tissues. We have measured tissue autofluorescence in human patients in vivo using different excitation wavelengths including 405 nm, 442 nm, and 488 nm by a specially designed optical multichannel analyzer which can be attached to a conventional bronchoscope. Contrary to the observation by Alfano et al., we did not find any difference in the shape of the fluorescence spectrum between normal and tumor tissues using these excitation wavelengths, in particular, there was no blue shift of the emission peaks. We observed a significant difference in the overall fluorescence intensity especially in the green region of the visible spectrum. A significant but a lesser decrease in the overall fluorescence intensity was also found in precancerous and non-cancerous lesions (dysplasia and metaplasia).

The decreased green fluorescence may be attributed to a reduced level of oxidized form of riboflavin. Riboflavin emits strongly in the green region and is believed to be predominantly responsible for the strong green fluorescence in normal human lung tissue. In the cancerous tissues, much less riboflavin was found (M.A. Pollack et al., *Cancer Res.* 2:739–743, 1942) and/or is present in the reduced state. This may account for the reduced autofluorescence in premalignant and malignant bronchial tissues.

Tests were conducted revealing examples of such decreased tissue autofluorescence for dysplastic bronchial tissue, and carcinoma in situ. It was determined that the main difference between abnormal and normal tissues is manifested by a greatly reduced fluorescence intensity in the region of the spectrum from 480 nm–600 nm. At wavelengths greater than approximately 635 nm, the tissue autofluorescence is approximately the same between abnormal and normal tissues. Tests were conducted using excitation light of 442 nm, 405 nm and 488 nm and abnormal tissue results were compared to normal tissue results. All of these data were obtained in vivo during standard fiber-optic bronchoscopy using the optical multichannel analyzer.

Because of the observed large decrease in the emitted fluorescence without a change in the spectral profile in the abnormal tissues, methods using rationing of two or more wavelengths that was originally described by Profio and coworkers and then studied in patients who have received fluorescent drugs such as Photoflin (Profo et al., *Med Phys.* 11:516–520, 1984) generally will not differentiate abnormal from normal bronchial tissues using autofluorescence alone.

We have invented and constructed an apparatus which exploits differences in autofluorescence intensity for the detection and delineation of the extent of abnormal areas in the human body, particularly the lung.

SUMMARY OF THE INVENTION

The present invention provides an imaging apparatus that uses autofluorescence characteristics of tissues to detect and delineate the extent of abnormal tissues in human patients in vivo. Capture and analysis of the autofluorescence images is achieved using a highly sensitive detector such as an image intensified CCD camera. A pseudo image is generated by sending one image to the red channel and one image to the green channel of an RGB video monitor. By capturing the two images simultaneously or sequentially within a few milliseconds, pseudo image generation in real time can be achieved. The pseudo images can clearly delineate the diseased tissue from the surrounding normal tissue.

Accordingly, the present invention provides an apparatus for imaging diseases in tissue comprising:

a light source for generating excitation light that includes wavelengths capable of generating characteristic autofluorescence for abnormal and normal tissues;

means for illuminating tissue with light that includes at least said excitation light thereby exciting the tissue to emit said characteristic autofluorescence;

collecting means for gathering emitted autofluorescence light from said tissue;

means for filtering said autofluorescence light into spectral bands in which said autofluorescence intensity for abnormal tissue is substantially different from normal tissue and said autofluorescence intensity for abnormal tissue is substantially similar to normal tissue;

optical means for intercepting said filtered autofluorescence light to acquire at least two filtered emitted autofluorescence images of the tissue; and display means for displaying said acquired images in such a manner as to delineate abnormal and normal tissue.

In a preferred embodiment, the apparatus of the present invention is used with a standard bronchoscope for imaging abnormal bronchial tissues.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIGS. 1A to 1D provide examples of autofluorescence spectrums at selected excitation wavelengths which indicate the difference between abnormal and normal tissue;

FIG. 2 is a schematic diagram showing the apparatus of the present invention useful for imaging abnormal lung tissue;

FIG. 3 shows details of the illumination module;

FIG. 4C shows a still further filtering and optical means in which a prism element is incorporated to allow two fluorescence images to be acquired simultaneously together with a reflected/scattered excitation light image.

DETAILED DESCRIPTION OF THE PREFERRED EMBODIMENT

While the preferred embodiment of the invention has been illustrated and described, it will be appreciated that various changes can be made therein without departing from the spirit and scope of the invention.

Figure 1B:
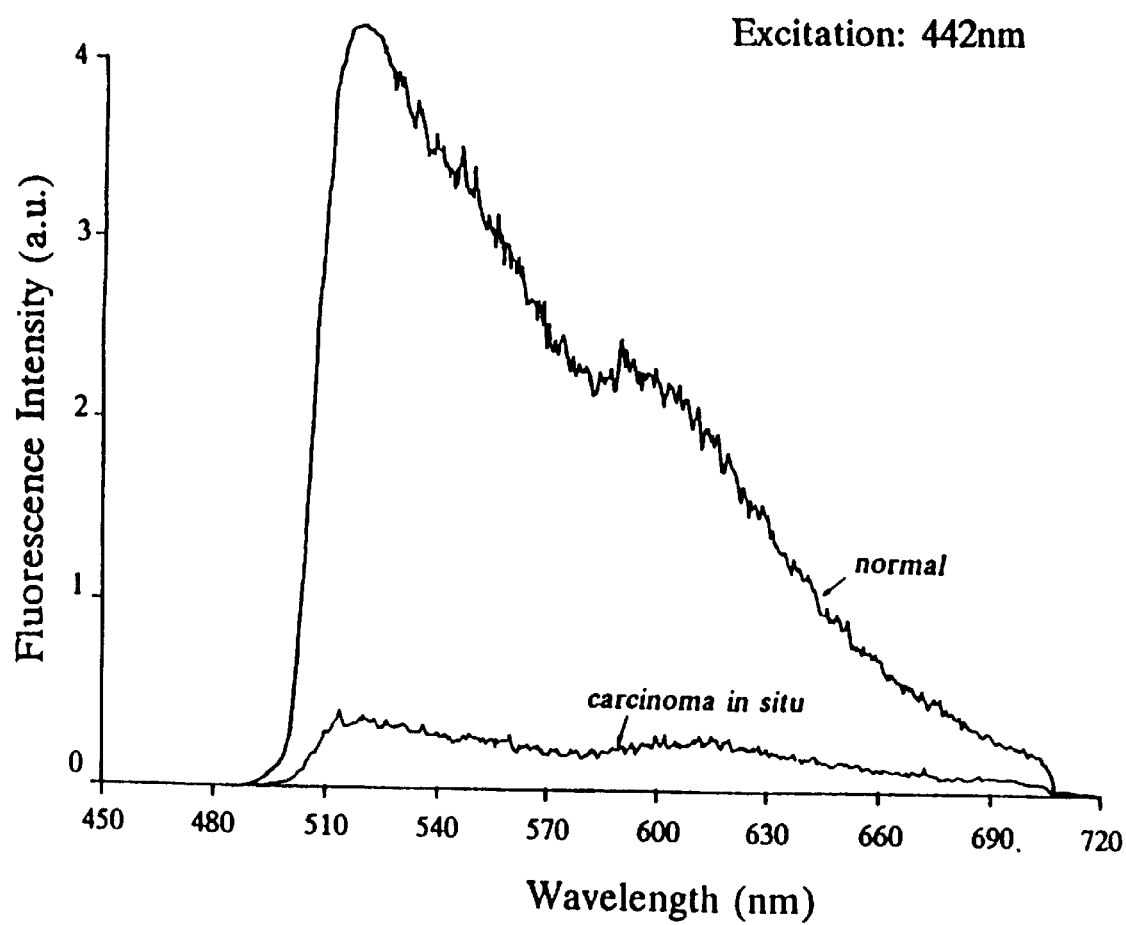

FIG. 1 shows examples of decreased tissue autofluorescence for dysplastic bronchial tissue and carcinoma in situ. The main difference between abnormal and normal tissues is manifested by a greatly reduced fluorescence intensity in the region of the spectrum from 480 nm–600 nm. At wavelengths greater than approximately 635 nm, the tissue autofluorescence is approximately the same between abnormal and normal tissues. For the results in FIGS. 1A and 1B, a 442 nm, Helium Cadmium laser light was used to excite the tissues. FIG. 1A shows tissue autofluorescence spectra of normal and dysplastic tissues and FIG. 1B shows a carcinoma in situ (CIS) lesion compared to the normal tissue of a different patient. Similar results were found when employing other excitation light, e.g., 405 nm, FIG. 1C, and 488 nm, FIG. 1D. In both cases carcinoma in situ patients are compared to their normal lung tissue. All of these data were obtained in vivo during standard fiber-optic bronchoscopy using an optical multichannel analyzer.

The apparatus of the present invention is designed to exploit the difference in fluorescence intensity in different regions of the spectrum to identify and delineate abnormal tissue.

The apparatus of the present invention adapted for use in examining bronchial tissues of the lung in patients is schematically illustrated in FIG. 2. As such, the apparatus is integrated with a conventional bronchoscope used for examining bronchial tissue of the lung.

There is a light source 1 for generating excitation light that includes wavelengths capable of generating characteristic autofluorescence spectra for abnormal and normal tissue. The light source 1 is shown in greater detail in FIG. 3 and preferably includes a laser light source 7 capable of producing excitation light at a selected desirable wavelength. A white light source such as an incandescent Xenon light source 8 can be used for white light illumination when desired. The laser light source 7 is used to generate pseudo images derived from tissue autofluorescence while the white light source is used to generate color images of reflected/scattered white light.

The light from each light source passes through synchronizing means that allow for alternate illumination of the tissue by the laser light and the white light source. In the embodiment illustrated in FIG. 3, the synchronizing means comprises blocking means in the form of electronically controlled shutters 9 and 13 associated with laser light source 7 and Xenon light source 8, respectively. When shutter 9 is open to allow laser light to pass, shutter 13 is closed to prevent passage of white light and vice versa. The light from the laser light source 7 passes through shutter 9 when open, a mirror with a pin hole 10, and a lens 11 which focuses the laser light onto means for illuminating the tissue with light comprising a conventional bronchoscope light guide 12. Light guide 12 conducts the excitation light to the tissue area under examination. The tissue, upon illumination with the laser light, emits its characteristic autofluorescence for abnormal and normal tissue. To generate regular white light illumination images, shutter 9 is closed and previously closed shutter 13 is opened to allow the light from Xenon light source 8 to pass through shutter 13. The white light is then filtered by a neutral density filter set 14, reflected by a mirror 15, and passes through a lens 16 which focuses the light onto bronchoscope light guide 12 after being reflected off mirror 10 and through lens 11. The neutral density filter set 14 is used to condition the light from the Xenon source such that it is of the appropriate intensity for the light sensors used in the apparatus. Thus the white light conducted to the tissue illuminates the tissue under examination. Light guide 12 ensures that the light is evenly dispersed over the area under examination.

In the present embodiment, the bronchoscope provides the collecting means to gather images in the form of the bronchoscope lens (not shown) which collects scattered and reflected light, or emitted autofluorescence light from within the lung for transmission out of the body by imaging bundle 2 of the bronchoscope. This collected light is transmitted to a focusing lens 21 of the bronchoscope ocular coupled to the imaging bundle.

From the ocular of the bronchoscope, the collected light enters the image acquisition module 3 which includes means for filtering the autofluorescence light and optical means for intercepting the filtered light. Various embodiments of image acquisition module 3 are possible.

Figure 4A:
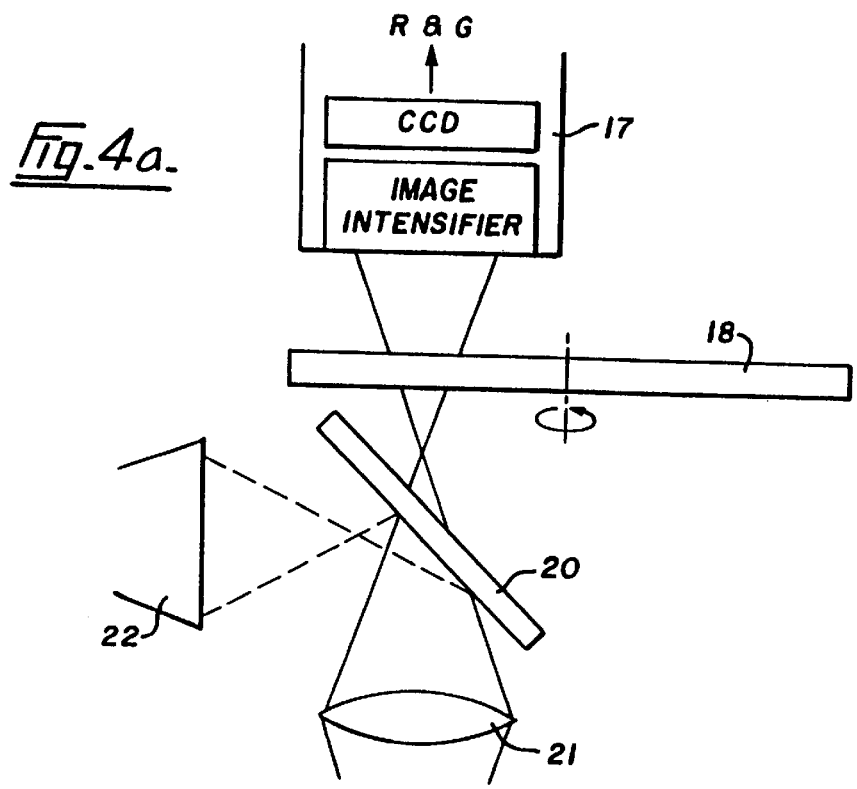
FIG. 4A shows the filtering and optical means of the present invention in which a single sensitive detector is used to acquire fluorescence images sequentially.

FIG. 4A illustrates an image acquisition module that includes filtering means and optical means that allow for acquisition of emitted autofluorescence images sequentially. In this embodiment, the means for filtering the autofluorescence light comprises a series of filters that are sequentially insertable into the path of the emitted autofluorescence light to generate a sequence of filtered autofluorescence images. Filter wheel 18 is provided and is rotatably mounted beneath the optical means of the image acquisition module. When laser excitation light 7 is used, it is necessary to filter the autofluorescence light generated into at least two spectral bands. In one spectral band, the autofluorescence intensity for abnormal tissue is substantially different from that of normal tissue and in the other spectral band, the autofluorescence intensity is substantially similar to that of normal tissue. For example, in accordance with the characteristic spectral bands indicated in FIGS. 1A to 1D for lung examination, filter wheel 18 would be fitted with two filters. For laser excitation light of 442 nm or 405 nm, a green filter of 500±20 nm and a red 630 nm long pass filter would be used. The green filter would filter the autofluorescence light into a spectral band in which the autofluorescence intensity for abnormal tissue is substantially different from that of normal tissue while the red long pass filter would filter the light into a spectral band in which the autofluorescence intensity is substantially similar for abnormal and normal tissue. The two filters are mounted in filter wheel 18 such that each covers one-half of the filter surface. By rotating filter wheel 18 at an appropriate speed, red and green filtered autofluorescence images can be captured sequentially by optical means in the form of a single highly sensitive detector 17 such as an image intensified CCD camera.

The foregoing image acquisition module also includes additional optical means for capturing reflected/scattered white light images when white light source 8 is providing illumination of the tissue. A movable mirror 20 is provided that is insertable into the path of the collected light transmitted by ocular lens 21. Mirror 20 is positionable to deflect white light into a color video camera 22 for acquisition of white light images. Necessarily, the movement of mirror 20 is controlled such that the mirror deflects the collected light into video camera 22 only when white light source 8 is providing illumination. Using white light source 8, color images can be generated on a color monitor in the same way as in conventional bronchoscopy. When laser light source 7 is illuminating the tissue, mirror 20 is removed from the light path to allow for filtering of the autofluorescence light and subsequent acquisition by detector 17.

Figure 4B:
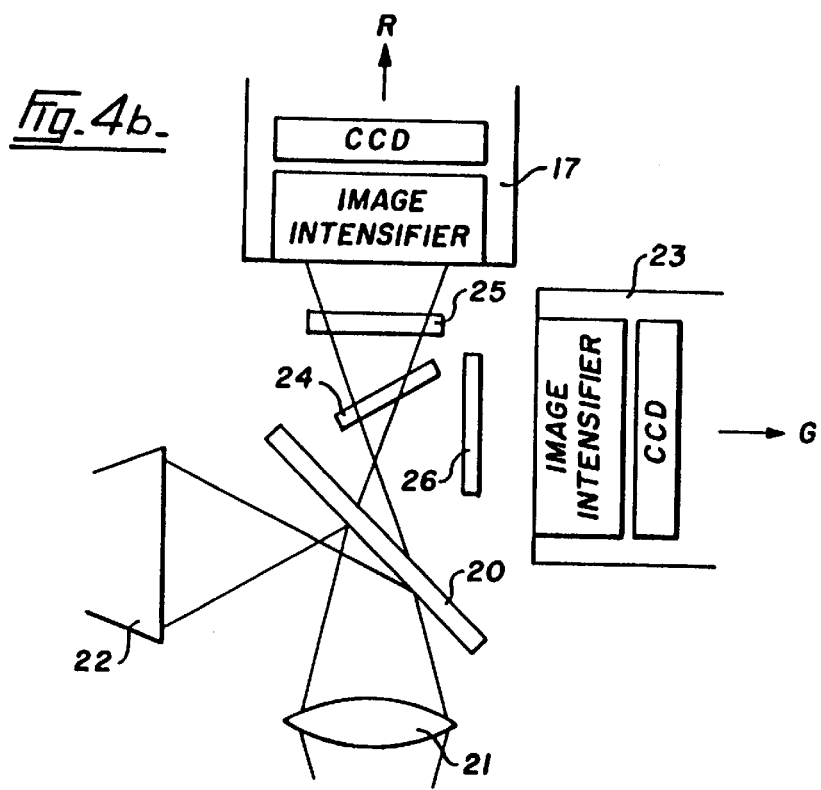
FIG. 4B shows alternative filtering and optical means m which fluorescence images are acquired simultaneously using two sensitive cameras.

FIG. 4B illustrates an alternative arrangement of image acquisition module 3 in which the optical means comprises at least two photodetectors that acquire filtered autofluorescence images simultaneously. Each photodetector has associated filtering means. For simultaneous collection of autofluorescence images, filter wheel 18 of the embodiment of FIG. 4A is replaced by beam splitting means in the form of a dichroic mirror 24 which allows the red light >600 nm to pass but reflects the shorter wavelengths. In this case, additional filters 25 and 26 for exact selection of the desired autofluorescence light can be employed and the respective images are focused onto two independent, sensitive photodetectors such as image intensified CCD cameras 17 and 23. In FIG. 4, filter 25 is a red 630 nm long pass filter to further filter red light passed by dichroic mirror into a spectral band in which autofluorescence intensity is substantially similar for normal and abnormal tissue. Filter 26 is a green filter of 500±20 nm for filtering the autofluorescence light into a spectral band in which the autofluorescence intensity for abnormal tissue is substantially different from that of normal tissue. Images acquired by the image intensified CCD camera 17 and/or image intensified CCD camera 23 are fed into red and green input channels of an RGB color monitor 5 (FIG. 1).

As in the arrangement of FIG. 4A, reflected/scattered white light images created by white light source 8 are captured by a color camera 22 and are displayed directly onto the color monitor for visualization of the examined site using an identical movable mirror 20 insertable into the light path whenever white light source 8 is providing illumination.

FIG. 4C illustrates a further embodiment of an image acquisition module for use with the apparatus of the present invention. A prism element 27 is provided that simultaneously splits collected light into a plurality of directions. By alternating between laser light source 7 and white light source 8, it is possible to capture sequentially both autofluorescence images and white light images within a 33 millisecond cycle time, therefore allowing a view of white (broadband) light color images and pseudo fluorescence images at the same time on display means.

A specially developed camera with three photodetectors 28, 29 and 30 is provided. The prism 27 splits the collected light into three images which are then captured by the three separate detectors. Photodetectors 28 and 29 comprise CCD imaging devices that are provided with associated image intensifiers 37 and 38 and photodetector 30 is a regular CCD imaging device. Each photodetector has its own filter 32, 33 and 34, respectively, as well as an x,y,z micropositioner 31. Filters 32 and 33 are the same as in the previous embodiments: a 500±20 nm green filter 33, and a 630 nm long pass filter 33. CCD imaging device 30 has an associated broadband blue filter 34.

As best shown in FIG. 2, associated camera control electronics 4 are such that they generate three image signals, a red signal produced by red filter 32 and intensified CCD imaging device 28, a green signal produced by green filter 33 and intensified CCD imaging device 29 and a blue signal produced by blue filter 34 and nonintensified CCD imaging device 30.

In all of the above embodiments, one can employ a specially designed CCD imaging device instead of an image intensified detector. For example, particularly when a lesser spatial resolution is required, several pixels of a sensitive scientific CCD detector can be electronically combined into a single very large pixel which allows very low signals to be detected.

All or some of the image signals produced by the various image acquisition modules of the present invention may be displayed directly on color monitor 5 or processed by image processing means prior to display. The apparatus of the present invention can switch between white (broadband) light illumination and laser illumination in one-thirtieth of a second.

Under laser illumination, the image acquisition module of FIG. 4C can collect autofluorescence images of the tissue over two selected areas of the spectra and a blue scattered/reflected excitation light image all simultaneously. These images can be combined either visually or mathematically via image processing means to make distinguishable the various tissue types present in the image. With white light illumination, the apparatus can collect red, green and blue reflected/scattered light images so as to make possible a regular color image of the tissues.

Furthermore, the color image can be combined with the autofluorescence blue laser illuminated images to enhance the detection, localization, and delineation of the various tissues.

For different tissues and/or diseases, a different combination of filters is employed to enhance the differences between normal and diseased tissues based on the characteristic emitted autofluorescence light of the diseased tissue under study.

As shown in FIG. 2, the present invention is preferably provided with image processing means in the form of an imaging board 35 associated with a computer 6 that controls and coordinates operation of the apparatus. Imaging board 35 allows images to be digitally captured if desired. Board 35 acts to digitize the filtered images provided by the image acquisition modules and enhance the digitized images by application of transformational algorithms to produce pseudo computed images in real time for display on video monitor 5. Alternatively, the digitized images can be stored in computer memory.

The pixel values in the digitized images can be used to calculate a value for each image pixel, using a mathematical transformation, so that all pixels covering the diseased tissue site are clearly different from those of the normal tissue. This process can be used to enhance the images, to enable the measurement of the degree of the disease, and make possible other applications and/or measurements.

Several mathematical algorithms have been developed that allow the creation of different computed pseudo images from the digitized emitted autofluorescence images and scattered/reflected light images, provided the autofluorescence images are captured over the spectral areas that are characteristic and appropriate for the specific tissue disease. Examples of appropriate mathematical algorithms that can be programmed and applied to the digitized images include hue, contrast and intensity functions, principal component decomposition algorithms, logarithm of differences, and subtraction algorithms, all of which delineate normal tissues from the diseased tissues.

One transformation which has been reported with tumor localizing drugs (A.E. Profio, *Med Phys.* 11:516–520, 1984) was found by us not to be useful for the imaging method; with the exception of large invasive cancers, it often fails to reveal the abnormal areas.

In a preferred embodiment of the present invention, digitization of images and image processing is not required. By employing color monitor 5 and the human visual system, it is possible to depict differences between the normal and diseased site as differences in perceived color.

When using the image acquisition module of FIG. 4B having two sensitive CCD cameras, one camera feeds the Red channel and the other feeds the Green channel of the RGB color monitor 5. The red tissue autofluorescence of the abnormal and normal bronchial tissues is approximately the same. The green tissue autofluorescence is dramatically decreased in the abnormal site compared to normal tissue. Therefore the abnormal site appears much less green and much more reddish and/or sandy colored compared to the surrounding normal tissue which looks bright green, as green fluorescence is much more dominant than red fluorescence in normal tissue. This preferred embodiment allows visualization of the diseased sites in real time without any processing of the images and is therefore very inexpensive.

The same result can be achieved using the single CCD camera and filter wheel of the image acquisition module of FIG. 4A. In this case, two sequential red and green fluorescence images must be electronically combined at video rates to be fed as red and green input signals for an RGB monitor.

Alternatively, two different spectral bands of tissue autofluorescence are acquired and interpreted as red and green signals for color display on a color monitor. This gives excellent pseudo images of inflamed tissue, dysplastic tissue and non-invasive cancer; clearly delineating these tissues from normal tissue. The decrease in diseased tissue autofluorescence, particularly in the green region, indicates the presence of the disease as well as the severity of the disease.

If tumor localizing drugs are used, the apparatus of the present invention can be used to visualize small and large tumors. For example, for drugs such as Photoflin (Porfimer sodium), the same filters can be used as the drug emits fluorescence at peak values of 630 nm and 690 nm. In this case all sites where the drug has localized will also be clearly delineated from the normal tissues.

Although the present invention has been described in some detail by way of example for purposes of clarity and understanding, it will be apparent that certain changes and modifications may be practiced within the scope of the appended claims.

The embodiments of the invention in which an exclusive property or privilege is claimed are defined as follows:

1. Apparatus for imaging diseases in tissue using autofluorescence comprising:
   a visible light source for generating excitation light that includes wavelengths that generate characteristic autofluorescence for abnormal and normal tissue;
   means for illuminating tissue with light from the visible light source that includes at least said excitation light thereby exciting tissue to emit said characteristic autofluorescence;
   collecting means for gathering reflected excitation light and emitted autofluorescence light from said tissue;
   a dichroic mirror positioned to receive the reflected excitation light and the emitted autofluorescence light gathered by the collecting means, the dichroic mirror operating to separate the spectral components of said autofluorescence light into at least a first spectral band including the reflected excitation light and the emitted autofluorescence light having wavelengths where an autofluorescence intensity for abnormal tissue is substantially different from normal tissue and a second spectral band different from said first spectral band including the emitted autofluorescernce light having wavelengths where an autofluorescence intensity for abnormal tissue is substantially similar to normal tissue;
   a first optical filter positioned to receive the light within the first spectral band, said first filter operating to remove the reflected excitation light from light within the first spectral band;
   a second optical filter positioned to receive the light within the second spectral band;

a first detector array for receiving the autofluorescence light within the first spectral band and for producing a first autofluorescence image of the tissue;

a second detector array for receiving the autofluorescence light within the second spectral band and for producing a second autofluorescence image of the tissue; and a color monitor that simultaneously displays the first and second autofluorescence images.

2. The apparatus of claim 1, in which the visible light source is a laser.

3. The apparatus of claim 1, in which the visible light source is a Xenon light source.

4. The apparatus of claim 1, wherein the dichroic mirror has a cutoff wavelength in the range of 600 nanometers.

5. The apparatus of claim 1, wherein the first optical filter is a band pass filter having a center frequency of about 500 nanometers and a band-pass of about ±20 nanometers.

6. The apparatus of claim 1, wherein the second optical filter is a red, long pass filter having a cutoff frequency of 630 nanometers.

7. The apparatus of claim 1, in which the means for illuminating tissue is a fiber-optic light guide.

8. The apparatus of claim 7, in which the collecting means is an imaging bundle and a focusing lens disposed within the fiber-optic light guide.

9. Apparatus for imaging diseases in tissue using autofluorescence comprising:

a visible light source for generating excitation light that includes wavelengths that generate characteristic autofluorescence for abnormal and normal tissue;

means for illuminating tissue with light from the visible light source that includes at least said excitation light thereby exciting tissue to emit said characteristic autofluorescence;

collecting means for gathering a reflected excitation light and an emitted autofluorescence light from said tissue;

means for separating the spectral components of the collected reflected excitation light and the emitted autofluorescence light gathered by the collecting means, into at least a first spectral band including the reflected excitation light and the emitted autofluorescence light having wavelengths where an autofluorescence intensity for abnormal tissue is substantially different from normal tissue and a second spectral band different from said first spectral band including the emitted autofluorescence light having wavelengths where an autofluorescence intensity for abnormal tissue is substantially similar to normal tissue;

a first optical filter positioned to receive the light within the first spectral band, said first filter operating to remove the reflected excitation light from light within the first spectral band;

a second optical filter positioned to receive the light within the second spectral band;

a first CCD camera for receiving the autofluorescence light within the first spectral band and for producing a first autofluorescence image of the tissue;

a second CCD camera for receiving the autofluorescence light within the second spectral band and for producing a second autofluorescence image of the tissue; and a color monitor that simultaneously displays the first and second autofluorescence image.

10. The apparatus of claim 9, wherein the means for separating the spectral components of the collected reflected excitation light and the autofluorescence light into the first and second spectral bands comprises a dichroic mirror.

11. The apparatus of claim 10, wherein the dichroic mirror has a cutoff wavelength of nearly 600 nanometers.

12. The apparatus of claim 9, wherein the means for separating the spectral components of the collected reflected excitation light and the autofluorescence light into the first and second spectral bands comprises a prism.

13. The apparatus of claim 9, in which the visible light source is a laser.

14. The apparatus of claim 9, in which the visible light source is a Xenon light source.

15. The apparatus of claim 9, wherein the first optical filter is a band pass filter having a center frequency of about 500 nanometers and a band-pass of about ±20 nanometers.

16. The apparatus of claim 9, wherein the second optical filter is a red, long pass filter having a cutoff frequency of 630 nanometers.

17. The apparatus of claim 9, in which the means for illuminating tissue is a fiber-optic light guide.

18. The apparatus of claim 17, in which the collecting means is an imaging bundle and a focusing lens disposed within the fiber optic-light guide.

19. Apparatus for imaging diseases in tissue using autofluorescence comprising:

a visible light source for generating excitation light that includes wavelengths that generate characteristic autofluorescence for abnormal and normal tissue;

a fiber optic light guide for illuminating tissue with light from the visible light source that includes at least said excitation light thereby exciting tissue to emit said characteristic autofluorescence;

collecting means for gathering reflected excitation light and emitted autofluorescence light from said tissue;

a dichroic mirror positioned to receive the reflected excitation light and the emitted autofluorescence light gathered by the collecting means, the dichroic mirror operating to separate the spectral components of said autofluorescence light into at least a first spectral band including the reflected excitation light and the emitted autofluorescence light having wavelengths where an autofluorescence intensity for abnormal tissue is substantially different from normal tissue and a second spectral band different from said first spectral band including the emitted autofluorescence light having wavelengths where an autofluorescence intensity for abnormal tissue is substantially similar to normal tissue;

a first optical filter positioned to receive the light within the first spectral band, said first filter operating to remove the reflected excitation light from light within the first spectral band;

a first detector array for receiving the autofluorescence light within the first spectral band and for producing a first autofluorescence image of the tissue;

a second detector array for receiving the autofluorescence light within the second spectral band and for producing a second autofluorescence image of the tissue; and a color monitor that simultaneously displays the first and second autofluorescence image.

20. The apparatus of claim 19, in which the visible light source is a laser.

21. The apparatus of claim 19, in which the visible light source is a Xenon light source.

22. The apparatus of claim 21, wherein the dichroic mirror has a cutoff wavelength in the range of 600 nanometers.

23. The apparatus of claim 22, wherein the first optical filter is a band pass filter having a center frequency of about 500 nanometers and a band-pass of about ±20 nanometers.

24. The apparatus of claim 19, further comprising a second optical filter positioned to receive the light within the second spectral band.

25. The apparatus of claim 24, wherein the second filter is a red, long pass filter having a cutoff frequency of 630 nanometers.

26. The apparatus of claim 19, in which the collecting means is an imaging bundle and a focusing lens disposed within the fiber-optic light guide.

27. Apparatus for imaging diseases in tissue using autofluorescence comprising:

a visible light source for generating excitation light that includes wavelengths that generaie characteristic autofluorescence for abnormal and normal tissue;

a fiber optic light guide for illuminating tissue with light from the visible light source that includes at least said excitation light thereby exciting tissue to emit said characteristic autofluorescence;

collecting means for gathering a reflected excitation light and an emitted autofluorescence light from said tissue;

means for separating the spectral components of the collected reflected excitation light and the emitted autofluorescence light gathered by the collecting means, into at least a first spectral band including the reflected excitation light and the emitted autofluorescence light having wavelengths where an autofluorescence intensity for abnormal tissue is substantially different from normal tissue and a second spectral band different from said first spectral band including the emitted autofluorescence light having wavelengths where an autofluorescence intensity for abnormal tissue is substantially similar to normal tissue;

a first optical filter positioned to receive the light within the first spectral band, said first filter operating to remove the reflected excitation light from light within the first spectral band;

a first CCD camera for receiving the autofluorescence light within the first spectral band and for producing a first autofluorescence image of the tissue;

a second CCD camera for receiving the autofluorescence light within the second spectral band and for producing a second autofluorescence image of the tissue; and a color monitor that simultaneously displays the first and second autofluorescence images.

28. The apparatus of claim 27, wherein the means for separating the spectral components of the collected reflected excitation light and the autofluorescence light into the first and second spectral bands comprises a dichroic mirror.

29. The apparatus of claim 28, wherein the dichroic mirror has a cutoff wavelength of nearly 600 nanometers.

30. The apparatus of claim 27, wherein the means for separating the spectral components of the collected reflected excitation light and the autofluorescence light into the first and secoirid spectral bands comprises a prism.

31. The apparatus of claim 27, in which the visible light source is a laser.

32. The apparatus of claim 27, in which the visible light source is a Xenon light source.

33. The apparatus of claim 32, wherein the first optical filter is a band pass filter having a center frequency of about 500 nanometers and a band-pass of about ±20 nanometers.

34. The apparatus of claim 27, further comprising a second optical filter positioned to receive the light within the second spectral band.

35. The apparatus of claim 27, wherein the second optical filter is a red, long pass filter having a cutoff frequency of 630 nanometers.

36. The apparatus of claim 25, in which the collecting means is an imaging bundle and a focusing lens disposed within the fiber optic-light guide.

* * * * *

UNITED STATES PATENT AND TRADEMARK OFFICE
CERTIFICATE OF CORRECTION

PATENT NO. : 5,769,792
DATED : June 23, 1998
INVENTOR(S) : B. Palcic et al.

It is certified that error appears in the above-identified patent and that said Letters Patent is hereby corrected as shown below:

| COLUMN | LINE | |
|---|---|---|
| 11 (Claim 27, | 13 line 4) | "generaie" should read --generate-- |
| 12 (Claim 30, | 19 line 4) | "secoirid" should read --second-- |
| 12 (Claim 35, | 30 line 1) | "27" should read --34-- |
| 12 (Claim 36, | 33 line 1) | "25" should read --35-- |

Signed and Sealed this

First Day of December, 1998

Attest:

BRUCE LEHMAN

Attesting Officer

Commissioner of Patents and Trademarks